United States Patent [19]

Jordan

[11] Patent Number: 5,381,075
[45] Date of Patent: Jan. 10, 1995

[54] METHOD AND APPARATUS FOR DRIVING A FLASHING LIGHT SYSTEMS USING SUBSTANTIALLY SQUARE POWER PULSES

[75] Inventor: Jeff P. Jordan, Kailua, Hi.

[73] Assignee: Unisyn, Waimanalo, Hi.

[21] Appl. No.: 33,771

[22] Filed: Mar. 18, 1993

Related U.S. Application Data

[63] Continuation-in-part of Ser. No. 855,306, Mar. 20, 1992.

[51] Int. Cl.$^6$ .......................................... H05B 37/00
[52] U.S. Cl. ................................. 315/200 A; 315/323; 315/185 R; 315/201; 307/41; 307/115
[58] Field of Search ............... 315/200 A, 323, 241 R, 315/201, 185 R; 307/41, 115

[56] References Cited

U.S. PATENT DOCUMENTS

| | | | |
|---|---|---|---|
| 3,876,907 | 4/1975 | Widmayer | 315/208 |
| 4,215,277 | 7/1980 | Weiner et al. | 315/323 |
| 4,713,586 | 12/1987 | Chiang | 315/323 |
| 4,749,916 | 6/1988 | Yamazaki et al. | 315/254 |
| 4,890,000 | 12/1989 | Chou | 315/323 |
| 4,942,303 | 7/1990 | Kolber et al. | 250/458.1 |
| 5,027,037 | 6/1991 | Wei | 315/323 |

FOREIGN PATENT DOCUMENTS 0084325  7/2783  European Pat. Off. .

OTHER PUBLICATIONS

Biotechnology & Bioengineering, Editor: Daniel I. C. Wang, vol. 28, No. 7, 1986.

Primary Examiner—Robert J. Pascal
Assistant Examiner—Reginald A. Ratliff
Attorney, Agent, or Firm—Christensen, O'Connor, Johnson & Kindness

[57] ABSTRACT

An enhanced method and apparatus for driving an immersed flashing light system used for enhancing algae growth is disclosed. The flashing light system includes a plurality of light source elements that are arranged to illuminate the algae. The light source elements are electrically connected to form "$\eta$" banks of light source elements. Power is supplied to each bank of light sources in a predetermined sequence at regular intervals to substantially evenly supply each bank of light source elements with a series of power pulses while maintaining a substantially continuous load on the power supply. The power pulses are substantially half cycles of a square wave.

5 Claims, 5 Drawing Sheets

METHOD AND APPARATUS FOR DRIVING A FLASHING LIGHT SYSTEMS USING SUBSTANTIALLY SQUARE POWER PULSES

FIELD OF THE INVENTION

The present application is a continuation-in-part of co-pending U.S. patent application Ser. No. 07/855,306 filed Mar. 20, 1992. The present invention relates to an apparatus for enhancing growth of photosynthetic organisms and, more particularly, to an improved flashing light system used in enhancing the photosynthesis of algae cultures.

BACKGROUND OF THE INVENTION

Mass algae cultures are generally cultivated in one of two ways. For lesser quantities, such as for use in laboratories, the algae cultures are produced in reactors using fluorescent lamps as a light source in gas sparging for agitation and gas exchange. Commercial quantities of algae cultures are generally produced in outdoor ponds using sunlight and paddle wheels for agitation.

It has been widely recognized in the literature that virtually all plants, including algae, make the most efficient use of light when the light is applied in pulses, commonly referred to as the "flashing-light effect." In outdoor ponds, various methods have been used to enhance natural turbulence in the flow of the medium for the purpose of exposing each algae to a flash of sunlight as it is momentarily near the surface. In laboratory systems using fluorescent lamps, the natural flicker of the lamps and the turbulence produced by the sparging gas also raise photosynthetic efficiency as a result of the flashing light effect.

However, prior studies have shown that the efficiency of light utilization for photosynthesis is much greater with shorter flash durations. In the mid-50s, researchers reported that sunlight flashes of one millisecond, separated by dark periods of 20 milliseconds, produced a growth that was similar to that observed under full continuous sunlight. These results were confirmed by other researchers who gave a broader theoretical interpretation to the results. The researchers report that photosynthesis is 15 times more efficient under ideal flashing light sources than it is under the full sunlight.

Artificially illuminated photosynthesis could certainly be made much more efficient and economically practical with the use of an efficient source of flashing artificial light. Many methods described in the prior art are unfortunately so inefficient that most of the economy is lost in the method of producing the flashes.

One conventional method of achieving a high frequency, short duration flashing light effect involves exposing an algae medium to a continuous light source while agitating the medium so that algae within the medium are effectively exposed to "flashes" of light. However, this level of agitation is prohibitively expensive for large-scale commercial operations.

Alternatively, other flashing light studies have been completed using a continuous light source that is cyclically shuttered to create a flashing effect. However, such mechanical creation of a flashing light is highly inefficient, since the radiant energy expended during the period when the light is shuttered is lost.

Several conventional systems have been developed in an attempt to use fluorescent or other gas discharge lamps for flashing-light sources. One such system, disclosed by U.S. Pat. No. 4,626,065 to Mori, utilizes a continuous light source, such as a fluorescent lamp or sunlight, to create a continuous beam of light that is distributed by a prism to an arrangement of photo radiators immersed in a tank. However, due to losses of radiant energy through the prism and photo radiators, and interruption of light utilization when the beam is switched from one photo radiator to another, the system is not highly efficient.

Other conventional flashing light systems have been developed that utilize gas discharge lamps, including fluorescent lamps, which are supplied with pulses of power from an intermittent power supply. For example, a system disclosed by U.S. Pat. No. 3,876,907 to Widmaver uses a grid control circuit to produce periodic direct current pulses that are supplied to a number of series connected gas discharge lamps. Again, however, this intermittent use of a power supply is not highly efficient.

In my co-pending U.S. patent application Ser. No. 07/855,306, a system including a tank for containing algae in a nutrient medium and a plurality of light source elements that are arranged to illuminate the algae medium is disclosed. The system operates on an AC power source and includes light source elements that are electrically connected to form "$\eta$" banks of light source elements. Power is supplied to each bank of light sources in a predetermined sequence at regular intervals to substantially evenly supply each bank of light source elements with a series of power pulses while maintaining a substantially continuous load on the power supply. The power pulses are typically half-sinusoids.

SUMMARY OF THE INVENTION

The present invention provides a flashing light system and method for enhancing algae photosynthesis by creating a highly efficient flashing light effect. The system includes a tank for containing algae in a nutrient medium and a plurality of light source elements that are arranged to illuminate the algae medium. The light source elements are electrically connected to form "$\eta$" banks of light source elements. A continuous DC power supply is switched by a controller among the banks of light sources in a predetermined sequence at regular intervals to substantially evenly supply each bank of light source elements with a series of power pulses while maintaining a substantially continuous load on the power supply. The power pulses are substantially half cycles of a square wave.

The system provides several advantages over prior art flashing light systems. By sequentially flashing a plurality of banks of lamps, a continuous load is placed on the power source, thereby continuously consuming power. Further, by providing a continuous load to the power source, transient and high frequency feed back voltages are not returned to the power source. Moreover, by providing a square wave power pulse to each bank of lights, the efficiency of the lamps is increased.

BRIEF DESCRIPTION OF THE DRAWINGS

The foregoing aspects and many of the attendant advantages of this invention will become more readily appreciated in view of the following detailed description, when taken in conjunction with the accompanying drawings, wherein.

DETAILED DESCRIPTION OF THE PREFERRED EMBODIMENT

Figure 1:
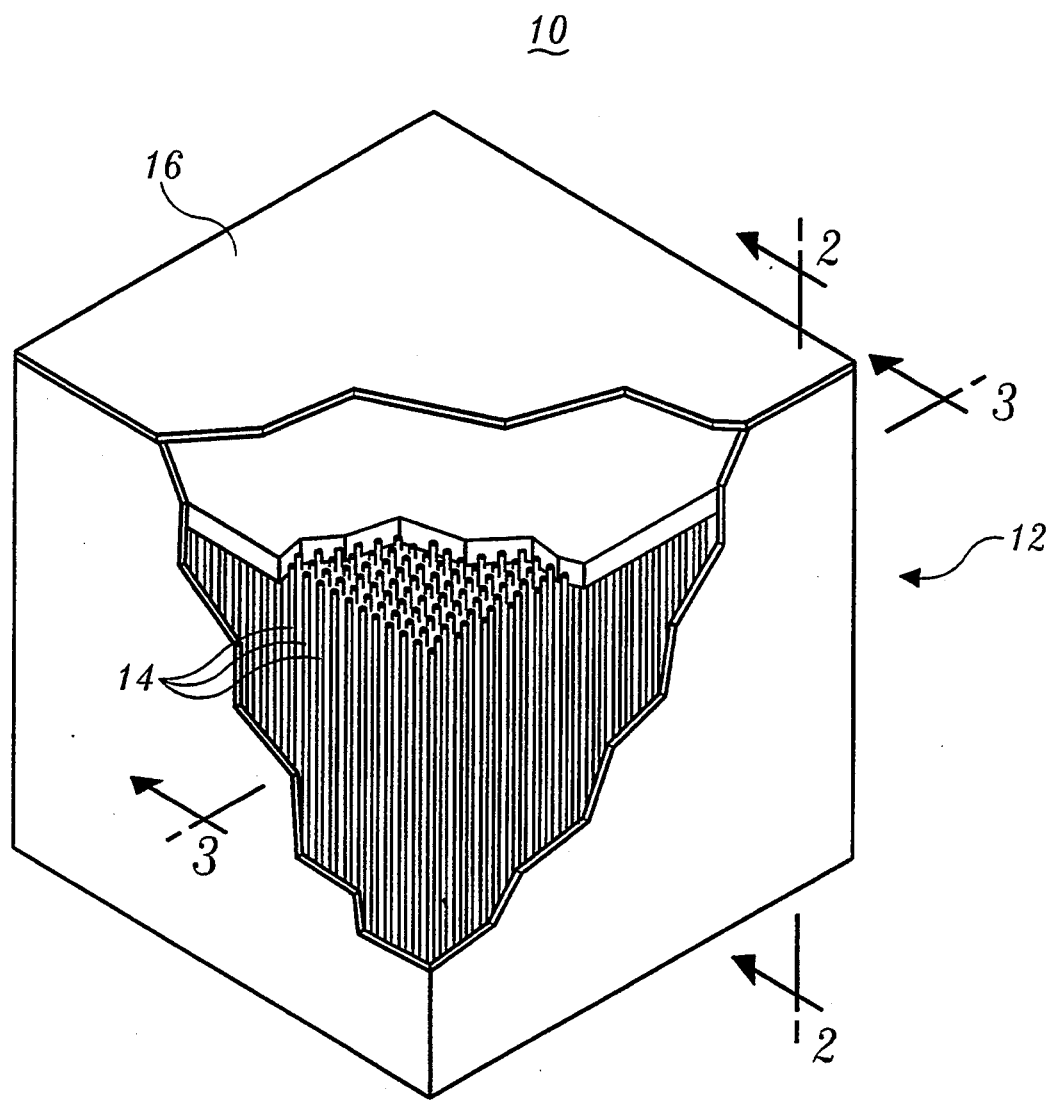
FIG. 1 is a perspective view of a flashing light system, with a portion of the tank wall and upper lamp fixture broken away.

The present invention provides a method and apparatus for driving flashing light systems having immersed fluorescent lights that are used for enhancing the growth of photosynthetic organisms. One such flashing light system 10 for enhancing algae photosynthesis is shown in FIG. 1. Although the present invention is described in conjunction with one particular flashing light system herein below described, the method of the present invention may be used on any flashing light systems that have lights immersed in conductive liquid. The system 10 includes a tank 12 for containing algae in a nutrient medium and a plurality of fluorescent lamps 14 arranged to intermittently illuminate the algae medium. The lamps 14 are electrically connected to form "η" banks, so that each bank of fluorescent lamps 14 produces a predetermined sequence of light flashes.

Flashing light is known to beneficially affect the rate of photosynthesis of many organisms, including leafy plants and other higher plant organisms. The system 10, which provides pulses of light in a highly efficient manner, can be adapted for enhancing the growth of various such higher plant organisms. However, the system 10 described herein is particularly adapted for enhancing the growth and photosynthesis of algae, such as *spirulina* and blue-green algae (cyanobacteria). Other types of algae can also be grown utilizing the system and method of the present invention, with the intensity and tinning of the light flashes produced by the system being adjusted accordingly, as described below.

The flashing light system provides for the efficient use of a continuously operating power supply that is switched sequentially among banks of light source elements, so as to provide intermittent power pulses to each bank of light source elements. The switching of the power supply to each bank of light source elements is accomplished by the driver circuit of the present invention. Each light source element thus receives power periodically, and exhibits a flashing light effect, while the power supply is placed under a substantially constant load.

Although the system 10 described herein utilizes fluorescent lamps 12, other light source elements, including other gas discharge lamps such as sodium vapor or metal halide lamps, could be utilized. However, fluorescent lamps have been found particularly well suited due to the linear distribution of the light produced therefrom. Further, fluorescent lamps are most efficient at operating temperatures corresponding to those required for many commercially significant algae, i.e. at about 95 to 100 degrees Fahrenheit. Conventional fluorescent lamps create mercury vapor arcs, which emit ultraviolet radiation that strikes phosphors coated on the inside of the lamp tube, producing a flash of light.

As shown in FIG. 1, the fluorescent lamps 14 are immersed in the nutrient medium for a more efficient transfer of light, because light reflection off the surface of the algae medium is eliminated, thereby reducing loss of light intensity. Over time, the outer surfaces of the immersed fluorescent lamps 14 may become fouled or clouded with algae. Thus, the medium may periodically need to be drained from the tank 12, followed by cleaning with caustic soda to remove the algae film. Alternatively, a scraper can be utilized to periodically cleanse the outer surface of the fluorescent lamps 14, as discussed below.

Figure 2:
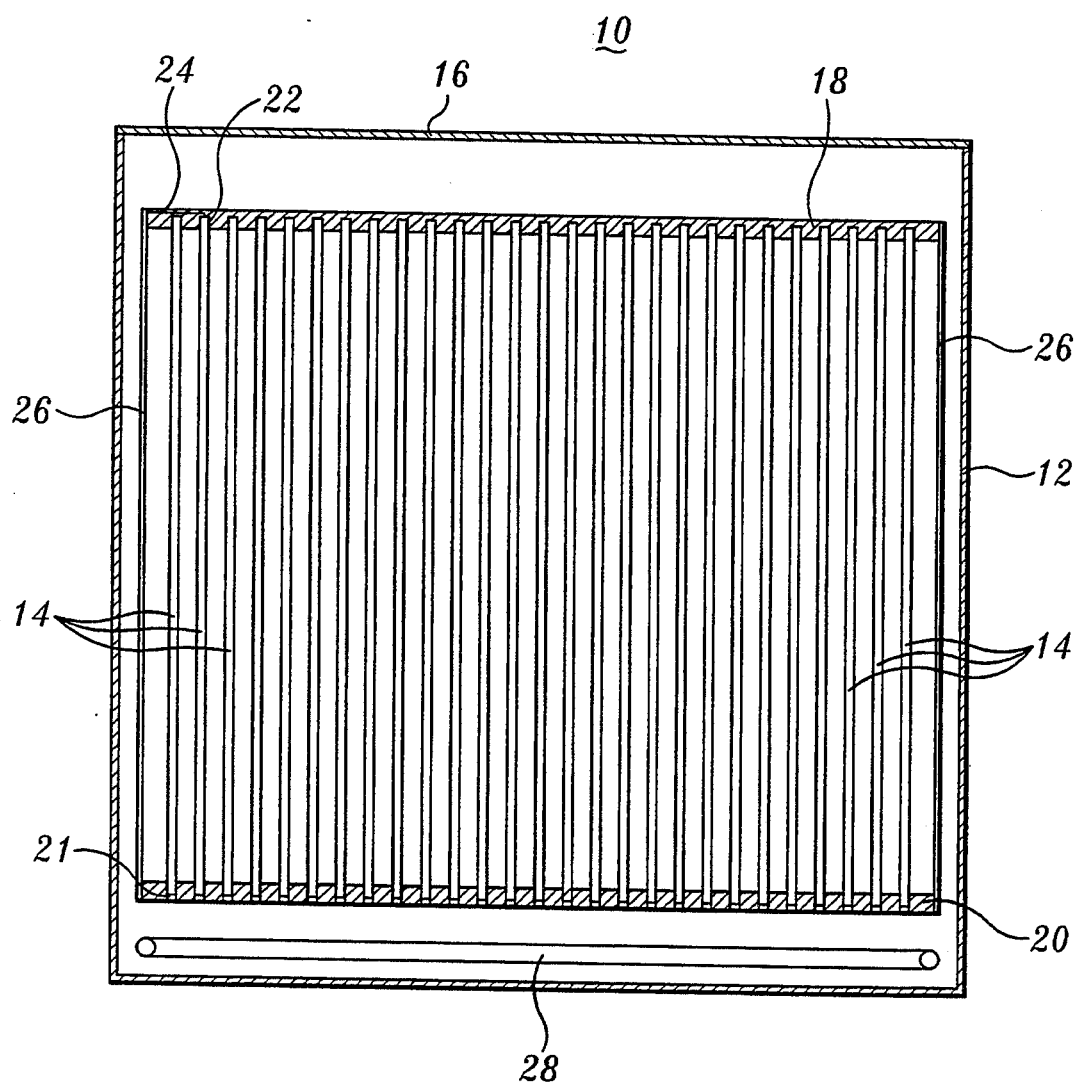
FIG. 2 is a cross-sectional view of the flashing light system taken substantially along a line 2—2 in FIG. 1.

Details of the mechanical construction of the system 10 shall now be described with reference to FIGS. 1 and 2. The tank 12 is covered by a cover 16. The fluorescent lamps 14 are preferably vertically disposed within the tank to minimize the effect of buoyancy on the lamps, and to facilitate low-energy gas-lift mixing. Referring to FIG. 2, the lamps 14 are mounted endwise a horizontal upper fixture 18 and a parallel lower fixture 20, each made of a corrosion resistant rigid material, such as a polyamide, a fiber reinforced thermosetting plastic, or resin coated plywood. The lower fixture 20 includes a plurality of transverse through apertures 21, arranged in a predetermined pattern, through which the lamps 14 are inserted.

The lamps are slid upwardly through the apertures in the lower fixture 20 until the plugs on the upper ends of the lamps are received in a corresponding socket 22 formed within the upper fixture 18 and sealed in place with a suitable sealant, such as silicone rubber. Electrical wiring 24 is laid within cavities formed within the upper portion of the upper fixture 18, and is soldered or otherwise electrically connected to the lamp 14 plugs. The wiring 24 is then encapsulated with any suitable sealant, such as an elastomeric silicon rubber or other dielectric material. A similar arrangement (not shown) is provided for electrically connecting to the plugs on the lower ends of the lamps 14. The upper fixture 18 bears the buoyant force of the lamps 14, and thus must be braced by a suitable structure (not shown) to the walls of the tank 12, or must be counterweighted. The upper fixture 18 and lower fixture 20 are maintained in spaced parallel relationship by vertical reinforcing members 26 secured at selected locations about the perimeter of the fixtures 18 and 20.

Still referring to FIG. 2, a conventional sparging tube 28 for introducing gas, such as compressed air, into the medium for agitation and exchange of gas by-products is positioned below the lower fixture 20, adjacent the bottom of the tank 12. The system 10 may also include a conventional heat exchanger (not shown) to maintain the medium at the temperature desired for optimal growth of the algae, and to absorb any excess heat produced by the lamps 14.

Depending on the particular algae and conditions being utilized, it may be necessary to utilize a traveling scraper to periodically cleanse algae film from the outer surfaces of the lamps 14. A suitable scraper (not shown) may include a horizontally oriented wiper plate having a number of apertures corresponding to the location of the lamps 14. The wiper plate can be located between the upper fixture 18 and lower fixture 20 prior to inserting the lamps 14. When the lamps are installed, they are inserted through a corresponding aperture in the wiper plate, and then into the socket 22 in the upper fixture 18. The traveling scraper can be mounted on and guided by the vertical reinforcing members 26, and can be periodically passed up and down along the length of the fluorescent lamps to clear the lamp extensions as needed. The scraper may be powered either manually or by a conventional motor.

Figure 3:
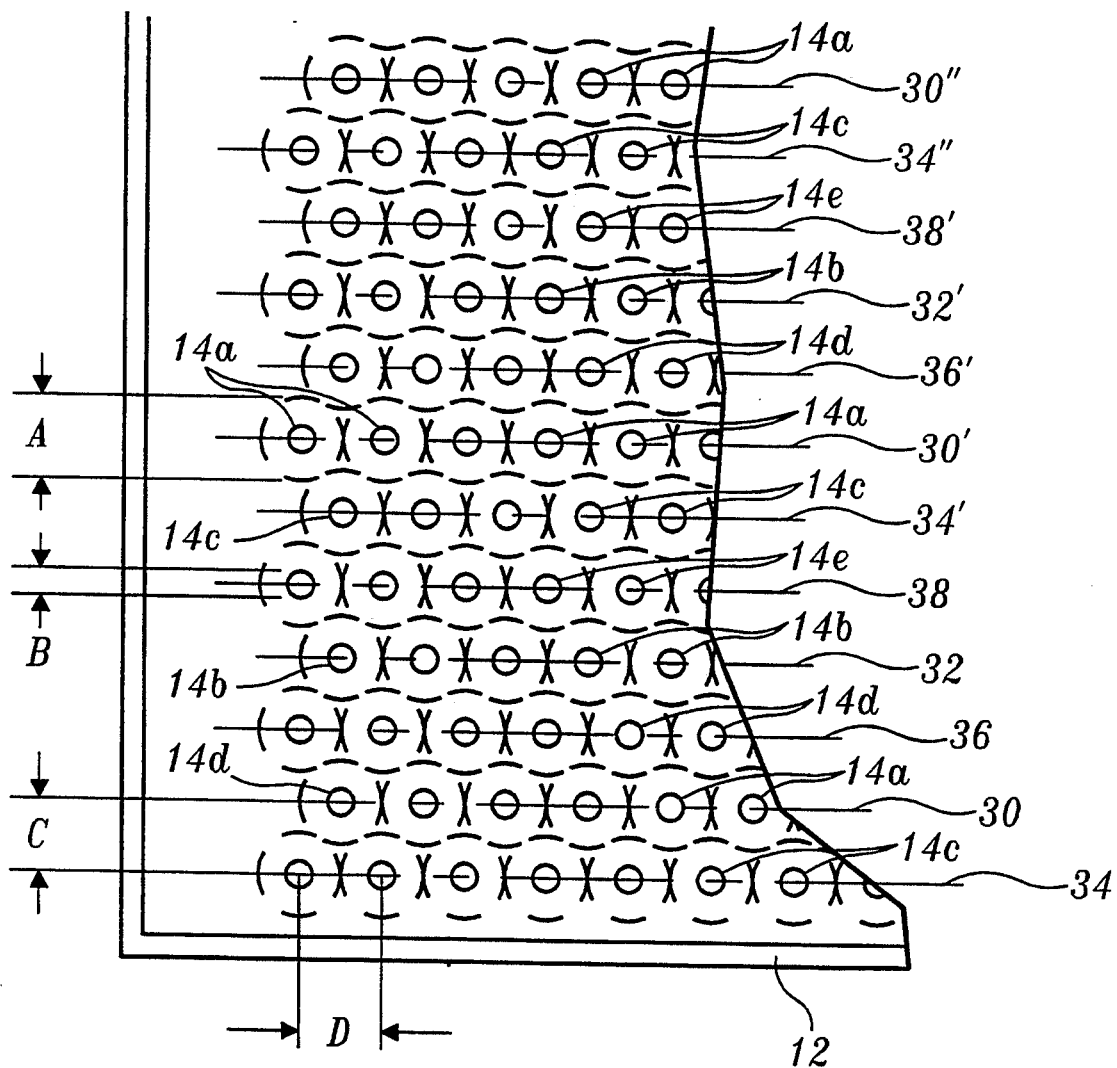
FIG. 3 is a partial cross-sectional view of the system taken substantially along a line 3—3 in FIG. 1, showing individual fluorescent lamps connected in five banks and arranged in planar rows, the diameter "B" of the individual lamps, the center-to-center spacing "C" between rows of lamps, and the diameter "A" of the illuminated zone around the lamps.

Referring now to FIG. 3, the fluorescent lamps 14 of the system 10 are electrically connected to form subgroups, or banks. The lamps 14 of each bank are connected together in series, and selected banks are electrically connected together in parallel. Power is initially supplied to all of the lamps 14 within a first bank, followed by switching of the power by the driver circuit of the present invention to supply all of the lamps 14 within a second bank, followed by switching to a third bank. Thereafter three or more banks or groups of banks are sequentially energized in a predetermined sequence. As each bank of lamps 14 is energized, the lamps 14 in that bank produce a short flash of light.

The sequential energization of the lamps results in each bank of lamps 14 producing a plurality of intermittent flashes. Thus, the system utilizes a continuous source of power that is switched sequentially among a plurality of banks of lamps. While each bank of lamps receives power only intermittently, the power supply sees a continuous, single load. Each subsequent bank of lamps 14 coming on-line provides a reactive energy path for the bank of lamps 14 going off, so that a continuous current path is created.

Referring to FIG. 3, the lamps 14 are arranged vertically and parallel to each other in rows. The individual lamps 14 within any given row are spaced evenly from each other by a center-to-center distance "D", while adjacent rows of lamps 14 are spaced a lamp center-to-lamp center distance "C" from each other. By way of example, FIG. 3 illustrates a suitable lamp layout pattern for use when the lamps 14 are connected to form five banks of lamps. Layout patterns for other numbers of banks are similar, as will be readily apparent. The lamps 14 in each bank are arranged in one or more rows, with all of the lamps in each of the rows of a particular bank being electrically connected in series. When each bank includes lamps arranged in a plurality of rows, the various rows of the banks may be interspersed.

For example, referring to FIG. 3, a plurality of lamps 14a are connected in series to form a first bank, and are arranged in spaced-apart planar rows 30, 30', 30'', etc. Lamps 14b are series connected to form a second bank of lamps, and are arranged in planar rows 32, 32', etc. Similarly, lamps 14c, 14d, and 14e are connected to form third, fourth, and fifth banks, respectively, and are arranged in rows(34,34', . . . ), (36, 36', . . . ), and(38,38', . . . ), respectively. The various planar rows 30-38 are vertically disposed and parallel to each other.

The rows of any two sequential banks are separated by at least one other row from another bank of lamps 14, so as to avoid sequential flashing of any two adjacent rows of lamps 14. For example, in FIG. 3, the lamps 14a of the first bank, arranged in planar rows (30, 30'. . . ), and the lamps 14b of the second bank, arranged along planar rows (32, 32'. . . ), are separated by lamps 14d of the fourth bank of lamps, arranged along planar rows (36, 36'. . . ). Likewise, the lamps 14b of the second bank, arranged along planar rows (32, 32'. . . ), and the lamps 14c of the third bank, arranged along planar rows (34, 34'. . . ), are separated by lamps 14e of the fifth bank, arranged along planar rows (38, 38'. . . ).

Standard conventional fluorescent lamps 14 have a tube diameter "B" of approximately 1.5 inches. By way of example, a suitable arrangement for lamps 14 used in the present system 10 for enhancing the growth of spirulina algae cultures involves the spacing of the individual lamps 14 within any given row a distance "D" of about 4.0 inches apart, and the spacing of adjacent rows a distance "C" of about 3.5 inches apart. This is based on the finding that the light from each lamp 14 penetrates a radial distance of approximately 1.25 inches into the algae medium, providing a total illuminated zone of diameter "A" equal to about four inches. By virtue of individual lamps in adjacent rows being staggered relative to each other, the interstices between the lamps are assured of near saturation with light during flashing.

It should be readily apparent that the spacing C and D between individual lamps 14 will vary depending on the algae being cultured and the density of the particular culture. Practitioners of skill in the art will know, in view of the disclosure contained herein, to adjust the spacing so as to uniformly saturate more or less dense cultures. If the spacing is too narrow, more than one flashing source will illuminate each region, thereby doubling or tripling the effective flashing rate, and reducing efficiency. Moreover, if the spacing is increased too far, algae respiration losses predominate over photosynthesis. Thus the spacing is determined based on experimentation with a particular culture for optimum utilization of the flashing light produced by the lamps 14. The preferred spacing for the lamps 14 described above has been found to be approximately half the distance that would be used to separate immersed fluorescent bulbs in conventional, continuous light systems. This spacing thus results in a four-fold increase in the number of lamps utilized in the present system over that in a conventional continuous light system. Additional details of the three bank flashing light system is disclosed in co-pending U.S. patent application Ser. No. 07/855,306 herein incorporated by reference.

Figure 4:
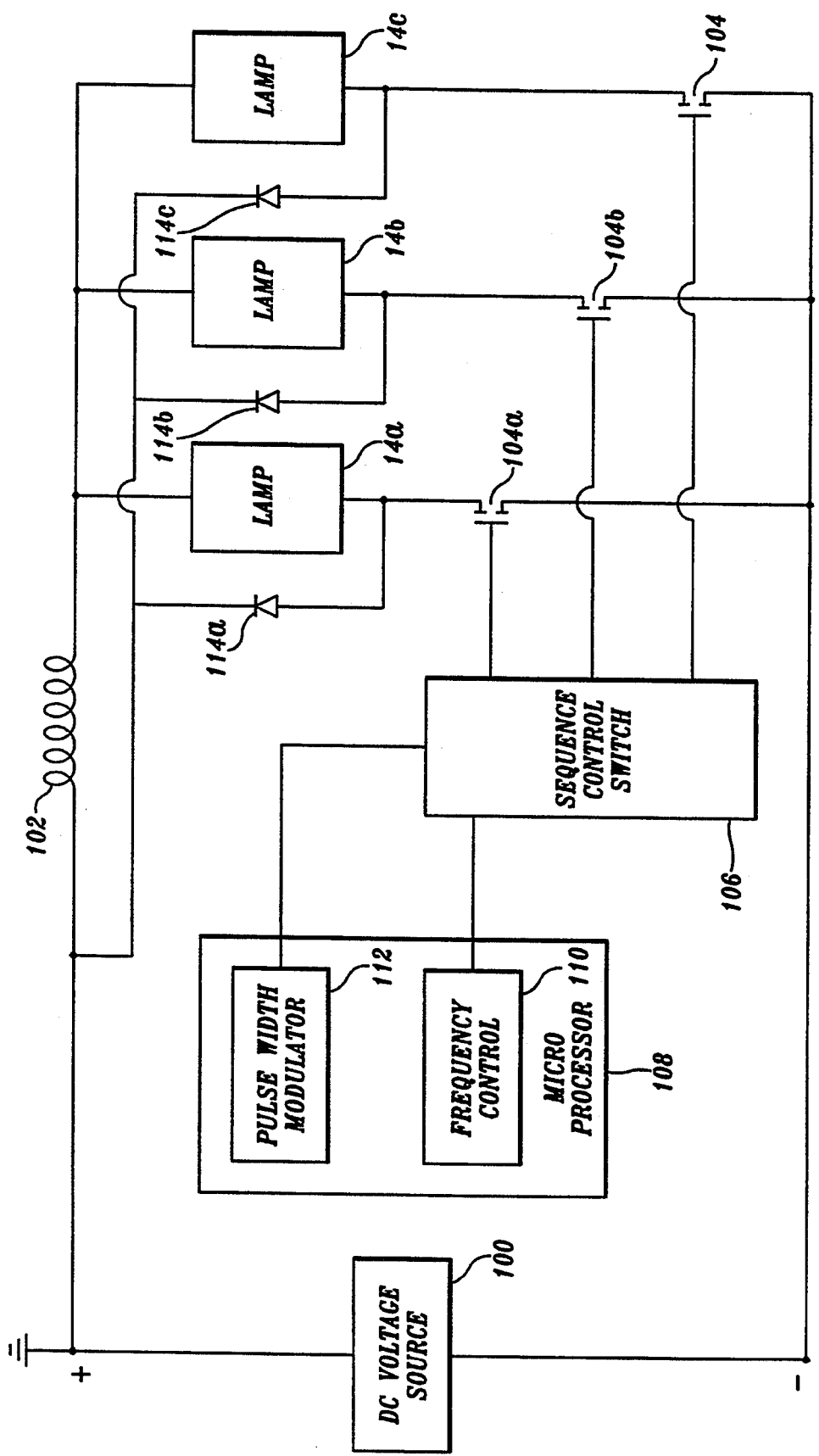
FIG. 4 is a schematic diagram of a driving circuit for the preferred embodiment of the present invention.

Although individual power supplies for each bank of lamps 14 could be utilized, the system makes more efficient use of energy by utilizing a single power supply that is operated substantially continuously to sequentially supply a plurality lamp banks 14a, 14b, and 14c with intermittent current pulses, so that lamps in each bank create a series of light flashes. As seen in FIG. 4, the preferred embodiment of the present invention includes a DC voltage source 100, a microprocessor 108, a sequence control switch 106, transistor switches 104a, 104b, and 104c, inductor 102, lamp banks 14a, 14b, and 14c, and return diodes 114a, 114b, and 114c. The circuit shown provides for the switching of power to three banks of lamps 14a, 14b, and 14c, respectively. It should be readily apparent that the circuit can be expanded for application to greater than three banks of lamps by including additional sets of components in parallel with those illustrated.

The DC voltage source 100 provides a constant voltage level output and can be a battery. Alternatively, the DC voltage source 100 can be a rectified three phase AC voltage source. As seen, the positive terminal of DC voltage source 100 is connected to the proximate terminal of inductor 102 and to ground. The negative terminal of DC voltage source 100 is connected to the common leads of transistors 104a, 104b, and 104c. The distal terminal of inductor 102 is connected to the upper terminal (as seen in FIG. 4) of lamp banks 14a, 14b, and 14c. Completing the circuit, the lower terminal of lamp banks 14a, 14b, and 14c is connected to the negative terminal of DC voltage source 100 through transistor switches 104a, 104b, and 104c, respectively. As will be described in greater detail below, transistor switches 104a, 104b, and 104c are controlled by sequence control switch 106 to allow current to flow through lamp banks 14a, 14b, and 14c in a sequential manner. Return diodes 114a, 114b, and 114c are connected to the positive terminal of DC voltage source 100 and the lower terminal of lamp banks 14a, 14b, and 14c, respectively.

Sequence control switch 106 is connected to and operative to control transistor switches 104a, 104b, and 104c so as to allow current to flow through the lamp banks sequentially. In particular, the transistors 104a, 104b, and 104c are sequentially turned on at predetermined intervals. As can be appreciated by those skilled in the art, when transistor switches are "on", current is allowed to flow through the transistor and when the transistor switches are "off", current is not allowed to flow through the transistor. Thus, only the lamp bank having its transistor switch in the "on" position will have the full voltage of the power supply plus the inductor voltage across it. Once the "on" lamp is in the conducting mode, the inductor 102 will act to limit the current flowing through the lamp. Thus, part of the power supply voltage will be dropped across the inductor 102. In this state, only the lamp bank having its transistor in the "on" position will have current flowing therethrough, thereby emitting light. When the transistor of the lamp bank is then switched to the "off" position, the inductor 102 will drive current briefly through the lamp bank and its return diode. For example, assuming that transistor switch 104a is initially in the "on" position, current flows through lamp bank 14a. However, when transistor switch 104a is switched to the "off" position, inductor 102 will drive the current briefly through lamp bank 14a and return diode 114a. Thereafter, all current will flow through the lamp bank with its switch in the "on" position and no current will flow through the lamps with transistor switches in the "off" position.

During optimal operation, the sequence control switch 106 only turns one of the transistor switches 104a, 104b, and 104c on at one time. Thus, if transistor 104a is "on", then transistors 104b and 104c are "off". For the three bank system 10 of FIG. 4, a first power pulse is initially supplied to the first bank of lamps 14a. A "power pulse" is the current that is allowed to flow through a lamp bank when the lamp bank's transistor switch is in the "on" position. Further, because of the DC power supply 100, the power pulses approximate an ideal square wave. As will be seen below, the application of a square wave power pulse to the lamp banks results in considerable efficiency gains. After the first power pulse is supplied to the first lamp bank, the sequence control switch 106 is then switched to deliver the next power pulse to the second bank of lamps 14b, followed by switching to supply the power pulse to the third bank of lamps 14c. The sequence then repeats, so that the next power pulse is again delivered to the first bank of lamps 14a. This sequence is continued so that each of the three banks of lamps receives an equal pulse of power, corresponding to a flash proportion, or duty cycle, of ⅓. The theoretical duty cycle, as used herein, is defined as the time duration of a flash of light divided by the sum of the time duration of a flash of light plus the time duration of darkness between subsequent flashes of light.

The operation of sequence control switch 106 is controlled by microprocessor 108, which includes a frequency control 110 and a pulse width modulator 112. The frequency control and pulse width modulator 112 work in conjunction to control the frequency of the sequence control switch 106 and thus the flash interval of each lamp, which consists of one or more power pulses. The flash interval in measured as time and is dependent on the frequency of power pulses and the number of power pulses at each flash interval. In particular, $$FI = N_p \div f$$

where FI is the flash interval, f is the frequency of the power pulses, and $N_p$ is the number of power pulses in each flash interval. Each lamp is "off" during the time the current is sequentially switched through each of the other lamps. Thus, the dark time or transistor "off" time for each lamp bank is determined by the flash interval (FI) and the number of lamp banks in the circuit. In particular, $$DT = FI*(N_L - 1)$$

where DT is the dark time or "off" time and $N_L$ is the number of lamp banks in the circuit.

One important aspect of the present invention is the use of inductor 102 to "kick" the activation of the next lamp bank as the previous lamp bank turns off. In short, the use of inductor 102 increases the efficiency of the system by ensuring that each lamp bank is operating at maximum efficiency the full duration of its power pulse. Thus, while the system is operating, the current through the inductor 102 remains nearly constant, therefore indicating that the load on DC power supply 100 is nearly continuous and stable. The operation of inductor 102 to achieve this result can be seen by considering the sequential operation of each lamp bank. In particular, when the system is energized, transistor switch 104a is turned on by sequence control switch 106 to allow current to flow through lamp bank 14a. When transistor switch 104a is turned on, the current flowing through both the inductor 102 and lamp bank 14a begins to rise exponentially. When the current reaches the set-point, transistor switch 104a is operated by pulse-width modulation to maintain the current through the lamp near the set-point. Each time transistor switch 104a goes "off," the inductor 102 continues to drive current through the lamp 14a and the diode 114a. This control action is continued for the duration of the flash interval to maintain constant current through the lamp.

Next, after the predetermined flash interval, the sequence control switch 106 turns off transistor switch 104a at the end of a modulated pulse and turns on transistor switch 104b. Transistor switch 104b is maintained "on" until the current flowing through it reaches the set-point. It is then switched "off" and operated by pulse-width modulation as before to maintain constant current through the inductor 102 and lamp 14b. The process repeats itself after the predetermined power pulse has been applied to lamp bank 14b. The sequence control switch 106 simultaneously turns off transistor switch 104b and turns on transistor switch 104c.

The use of the inductor 102 and return diodes 114a, 114b, and 114c is especially useful when the lamp banks are comprised of fluorescent lamps. As is known in the art, fluorescent lamps generally require a large starting voltage in order to emit light. Moreover, fluorescent lamps typically require a substantial lag time from the application of voltage to the lamp and the emission of light. The role of the inductor 102 in passing the controlled current from one lamp bank to the next lamp bank can be seen by examining the voltages within the circuit. When current is flowing through the inductor 102, the lamp 14a that is currently "on," and the associated transistor switch 104a, the voltage from DC voltage source 100 is partitioned between the inductor 102 and the lamp 14a. Further, the inductor 102 limits the current from rising uncontrollably as the lamp 14a would allow. During this period, the inductor 102 is charging, as the voltage drop across the inductor 102 is causing an inductor-limited increase of current through the inductor 102 and the lamp 14a. When all of the transistor switches are "off," the inductor 102 discharges its energy by maintaining a decreasing current through the lamp that was last "on" and its associated return diode. When the inductor 102 is discharging its stored energy and all of the transistor switches are momentarily "off," the same voltage is present across each of the return diodes 114a, 114b, and 114c, since they are all in parallel. However, current will only flow through the lamp which arcing at the time the "on" transistor switch goes off. The other lamps are in the high impedance "off" or non-arcing state and would require twice as much voltage to strike an arc and go into a conductive state. In this way, the transistor in series with the "on" lamp can be used in a high frequency pulse-width modulated mode to precisely control the current through the "on" lamp. For example, the transistor switch associated with the "on" lamp may switch "on" and "off" ten times during the lamp's "on" interval.

At then end of the "on" lamp's flash interval, its transistor goes "off" and the next lamp's transistor switch goes "on." The voltage across the lamp bank that is being turned off is now the voltage generated by the inductor 102, which continues to drive current through the lamp that is going off and its associated return diode. However, the voltage across the lamp that is turning on is the sum of the voltage across the lamp that is turning off (the inductor 102 voltage) and the DC voltage source 100. This higher voltage across the lamp bank that it turning on quickly overcomes its arc threshold, causing it ionize and turn "on." Both lamps are instantaneously "on," but the voltage across the lamp that is turning on is greater than the lamp that is turning off by the amount of the DC voltage source 100. This large voltage difference results in a rapid shift of current from the lamp that is turning off to the lamp that is turning on. The total current is maintained constant by the inductor during this short transition interval. The foregoing process of using the inductor 102 utilizes energy from DC voltage source 100 most efficiently. In particular, all of the energy from DC voltage source 100 is consumed in the lamps 14a-c, either directly or after being stored briefly in the inductor 102.

It should be readily apparent to those of ordinary skill in the art that various alterations can be made to the circuitry described above in accordance with the current invention. Relative to conventional, continuously operated fluorescent lamps, the system and method of the present invention described above provides for the generation of discrete flashes of light of short duration and high intensity, occurring at a high frequency with a long period between individual flashes. It should be readily apparent that the frequency of the system, in combination with the inductance of the inductor as well of the phosphors used in the lamps, can be adjusted to produce longer or shorter flashes of light and different wavelengths, as desired for a particular algae culture or other photosynthetic organism.

In my co-pending application Ser. No. 07/855,306, the banks of lamps are powered by half-sinusoidal power pulses. As noted above, the present invention includes the use of an inductor to "kick" the next bank of lamps to ignition. Further, the use of square wave power pulses provides an added measure of efficiency. It has presently been discovered that the use of fluorescent lamps immersed in conductive liquid mediums results in the generation of electric currents in the medium. This undesirable effect is enhanced when the medium includes dissolved conductive salts. The effect is most pronounced at higher operating frequencies, particularly at frequencies greater than 1 kHz. The application of half sinusoids creates a changing current in the fluorescent lamps as the voltage of the half sinusoidal power pulse changes. The changing current in turn causes an induced magnetic field about each fluorescent lamp. It is well known that for an invariant load resistance, the current waveform is proportional to the voltage waveform. Thus, the current waveform flowing through the fluorescent lamps is proportional to the voltage waveform applied thereto. Exposure of the conductive medium to this magnetic field results in the inducement of a current in the medium, thus dissipating a non-negligible amount of energy.

To combat the energy losses resulting from this phenomena it has been discovered that the application of square wave power pulses that approximate an ideal square wave will minimize the energy loss. In that situation, the current flow through the fluorescent lights would only change on the leading edge of the square wave power pulse and on the trailing edge of the square wave power pulse. In the case of a square wave power pulse, for a given amount of energy delivered by a pulse, the change in voltage, and thus current flow, is minimized.

Figure 5:
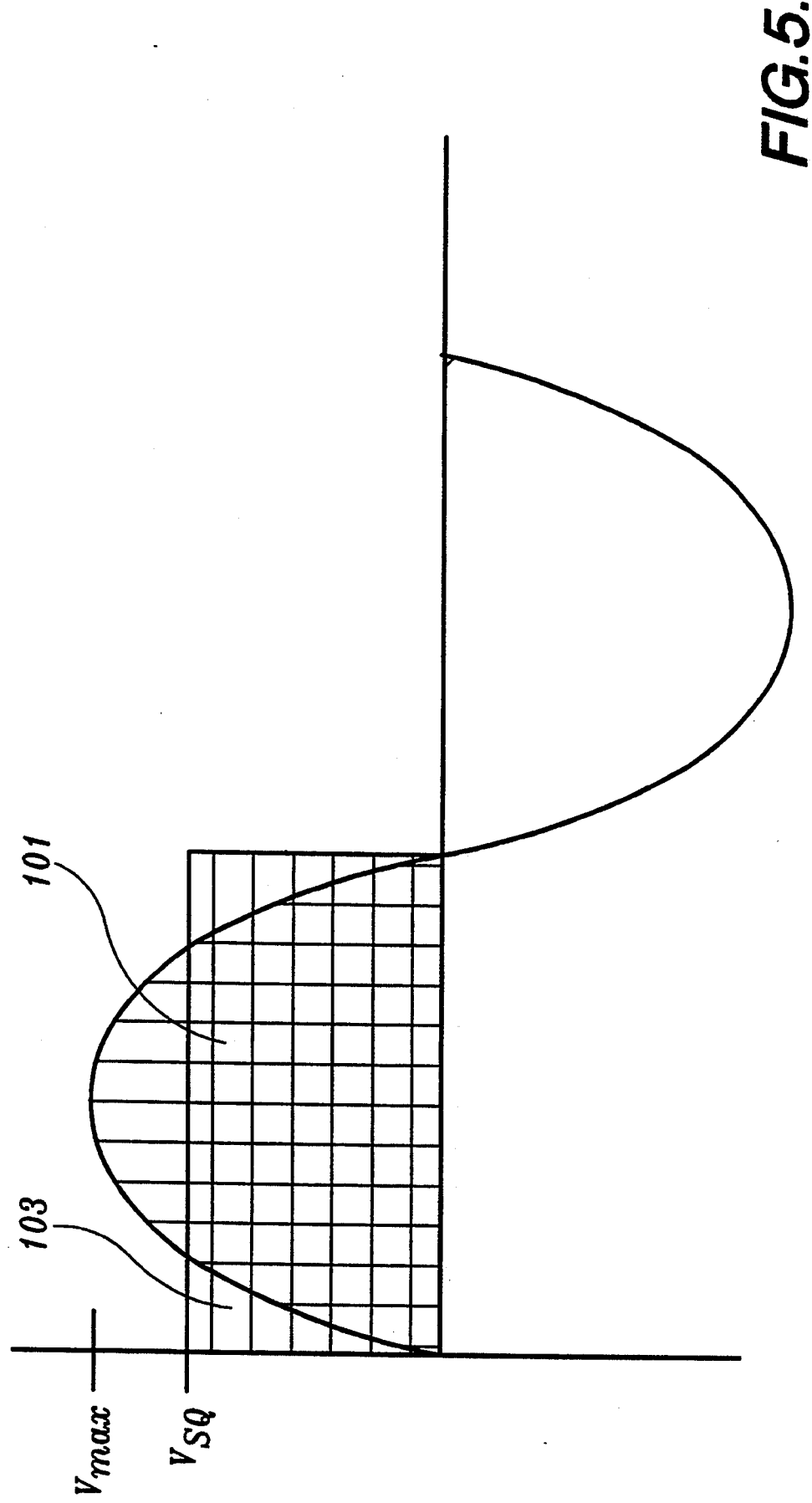
FIG. 5 is a diagram of a sinusoidal wave superimposed on a square wave that illustrates one advantage of the method of the present invention.

To see this result, as seen in FIG. 5, a half sinusoid power pulse 101 is superimposed onto a square wave power pulse 103 having the same frequency. Moreover, as is known in the art, the total energy supplied by the power pulse to a particular fluorescent light is proportional to the area under the power pulses 101 and 103. In the case of the half sinusoidal power pulse 101, the area is given by the integral of sin (x) over the period zero to $\pi$. Taking this integral, the energy supplied is proportional to $2*V_{max}$, where $V_{max}$ is the peak voltage level of the half-sinusoidal power pulse 101.

A square wave power pulse may supply an identical amount of energy with a lower variation in voltage. In order to supply an identical amount of energy, the square wave power pulse 103 should have a total area of $2*V_{max}$. The area of a square wave power pulse can be calculated as $\pi*V_{SQ}$, where $V_{SQ}$ is the maximum voltage of the square wave voltage pulse. Thus, to provide the identical amount of energy, the maximum voltage of the square wave power pulse is given as: $V_{SQ}=(2*V_{max})/\pi$. $V_{SQ}$ is clearly less than $V_{max}$. The lower maximum voltage of the square wave power pulse 103 in turn provides a lower maximum current flow through the fluorescent light. Because the fluorescent light undergoes a lesser variation in current, less energy is lost in the nutrient medium as a result of induced currents. An additional benefit by driving the fluorescent lamps with a square wave power pulse is that the life of the lamps are increased. With the lower voltage of the power pulse, lower current flows through the lamps providing extended life. For these reasons, it has been found that it is preferable to drive the flashing light system with a system providing a square wave power pulse, such as the system shown schematically in FIG. 4.

Another advantage of providing a square wave power pulse to the lamps is that the lamps are immediately brought up to efficient operating current. In particular, a fluorescent lamps output is proportional to the current flowing in the lamp. The current in the lamp is in turn proportional to the voltage applied to the lamp. With the use of a sinusoid voltage source, the current in the lamp requires a finite time for the sinusoid signal to reach a voltage level conducive to maximum efficiency. In contrast, the use of a square wave power pulse immediately drives the current flow through the lamp to optimal levels. Thus, the use of a square wave to drive fluorescent lamp increases the efficiency of the lamps themselves.

The above described system provides several advantages over prior art flashing light systems. First, by using the sequence control switch 106 to sequentially flash a plurality of banks of lamps, a continuous load is placed on the power source, thereby continuously consuming power. Further, by providing a continuous load to the power source, transient and high frequency feed back voltages are not returned to the power source. Second, by providing a square wave power pulse to each bank of lights, the efficiency of the lamps is increased. Lastly, by the use of the driving circuit shown in FIG. 4, and more particularly, the use of an inductor to "kick" the next bank of lamps into full maximum current, there is no loss of energy.

While the preferred embodiment of the invention have been illustrated and described, it will be appreciated that various changes can be made therein without departing from the spirit and scope of the invention. Therefore, it is intended that the scope of the letters patent granted hereon be limited only by the definitions contained in the appended claims and the equivalents thereof.

The embodiments of the invention in which an exclusive property or privilege is claimed are defined as follows:

1. A flashing light system for enhancing algae photosynthesis of algae in a nutrient medium, comprising:
   a plurality of light source elements that are arranged to illuminate the algae medium and that are electrically connected to form n banks of light source elements;
   a DC power supply for supplying power to said banks of light source elements;
   switching means for switching power among the banks of light source elements in a predetermined sequence to substantially evenly supply each bank of light source elements with a series of power pulses that cause current to flow through said bank of light source elements, said power pulses being substantially square waves; and
   means for routing current from a prior fired bank of light source elements when said prior fired bank of light source element is being turned off to a subsequent bank of light source elements that is being turned on, wherein said means for routing current is an inductor disposed between said DC power supply and said banks of light source elements.

2. The system of claim 1, wherein said switching means includes a microprocessor controlled sequence control switch and a transistor switch for each of said bank of light source elements.

3. The system of claim 2, wherein said microprocessor includes a frequency control for determining the frequency of said power pulses to each of said bank of light source elements.

4. The system of claim 2, wherein the light source elements comprise fluorescent lamps.

5. The system of claim 4, wherein the light source elements in each bank are arranged in rows, and the rows of light source elements of each bank are interspersed among the rows of light source elements of other banks.

* * * * *